(12) United States Patent
Eicher et al.

(10) Patent No.: US 8,921,622 B2
(45) Date of Patent: *Dec. 30, 2014

(54) PROCESS FOR DEHYDROFLUORINATING HYDROCHLOROFLUOROALKANES AND PRODUCTS OBTAINED THEREBY

(75) Inventors: Johannes Eicher, Sehnde (DE); Ercan Uenveren, Hannover (DE); Erhard Kemnitz, Berlin (DE)

(73) Assignee: Solvay SA, Brussels (BE)

( * ) Notice: Subject to any disclaimer, the term of this patent is extended or adjusted under 35 U.S.C. 154(b) by 0 days.

This patent is subject to a terminal disclaimer.

(21) Appl. No.: 13/637,989

(22) PCT Filed: Mar. 31, 2011

(86) PCT No.: PCT/EP2011/054979
§ 371 (c)(1),
(2), (4) Date: Sep. 28, 2012

(87) PCT Pub. No.: WO2011/121057
PCT Pub. Date: Oct. 6, 2011

(65) Prior Publication Data
US 2013/0023703 A1 Jan. 24, 2013

Related U.S. Application Data

(60) Provisional application No. 61/320,421, filed on Apr. 2, 2010.

(51) Int. Cl.
*C07C 17/25* (2006.01)
*C07C 21/18* (2006.01)

(52) U.S. Cl.
CPC .......... *C07C 21/18* (2013.01); *C07C 17/25* (2013.01)
USPC .......... 570/156; 570/155; 570/226; 570/227; 570/230

(58) Field of Classification Search
USPC .................. 570/155, 156, 226, 227
See application file for complete search history.

(56) References Cited

U.S. PATENT DOCUMENTS

| 5,243,103 A | 9/1993 | Lerot et al. |
| 7,074,434 B2 | 7/2006 | Lambert et al. |
| 2006/0052649 A1 * | 3/2006 | Kemnitz et al. ............ 570/166 |
| 2007/0129579 A1 * | 6/2007 | Wang et al. ............... 570/155 |

FOREIGN PATENT DOCUMENTS

| EP | 1666411 A1 | 6/2006 |
| WO | WO 2004060806 A1 | 7/2004 |
| WO | WO 2007053673 A2 | 5/2007 |
| WO | WO 2008043720 A2 | 4/2008 |
| WO | WO 2009010472 A1 * | 1/2009 |
| WO | WO 2010055146 A2 | 5/2010 |
| WO | WO 2010060868 A1 | 6/2010 |
| WO | WO 2011121058 A1 | 10/2011 |

OTHER PUBLICATIONS

Kemnitz, Erhard, et al—"Amorphous metal fluorides with extraordinary high surface areas", 2003, Angewandte Chemie, vol. 115, Issue No. 35, pp. 4383-4386, 6 pgs.
Rudiger, S., et al—"The fluorolytic sol-gel route to metal fluorides—a versatile process opening a variety of application fields", 2008, Perspective, The Royal Society of Chemistry, Dalton Trans. vol. 7; Issue No. 9; pp. 1117-1127; 11 pgs.
Haszeldine, R. N., et al—"Reactions of Fluorocarbon Radicals. Part XV. Synthesis and Hydration of 1 : 1 : 1-Trifluorobut-2-yne", 1954, J. Chem. Soc., pp. 1261-1264, XP002635098; 4 pgs.

* cited by examiner

*Primary Examiner* — Jafar Parsa
*Assistant Examiner* — Medhanit Bahta

(57) ABSTRACT

A process for the selective dehydrofluorination of hydrochlorofluoroalkanes and novel hydrochlorofluoroalkenes is described wherein an effective amount of a catalytically active metal compound is applied which is selected from the group consisting of $AlF_{3-\delta}$, $MgAl_xF_{2+3x-\delta}$ and $MgZr_yF_{2+4y-\delta}$, wherein x and y have, independently of one another, values in the range of from 0 to 0.33 and $\delta$ has a value in the range of from 0 to 0.1. Certain hydrofluorochloroalkenes are also described, as well as their use as intermediates in chemical reactions.

11 Claims, No Drawings

PROCESS FOR DEHYDROFLUORINATING HYDROCHLOROFLUOROALKANES AND PRODUCTS OBTAINED THEREBY

This application is a U.S. national stage entry under 35 U.S.C. §371 of International Application No. PCT/EP2011/054979 filed Mar. 31, 2011, which claims priority to U.S. provisional patent application No. 61/320,421 filed Apr. 2, 2010, the whole content of this application being incorporated herein by reference for all purposes.

The present invention relates to a process for dehydrofluorinating hydrochlorofluoroalkanes, novel hydrochlorofluoroalkenes obtained thereby and the use thereof in the manufacture of hydrofluoroalkanes and hydrofluoroalkenes.

WO 2009/010472 discloses a process for the preparation of halogen containing alkenes over metal fluoride catalysts. Hydrochlorofluoroalkanes are also mentioned as suitable starting materials, but in those cases dehydrochlorination is observed. As chlorine atoms are the better leaving group compared to fluorine atoms, dehydrofluorination does not normally take place as long as dehydrochlorination is possible, which poses certain limitations on the availability of hydrochlorofluoroalkenes Unsaturated hydrochlorofluoroalkenes have been described in the literature and have found use e.g. in cleaning compositions for surfaces or as useful intermediates in the manufacture of hydrofluorocarbons.

WO 2007/053673 discloses in Table 4 and in the specification a number of compounds of this group and describes in general terms processes for their manufacture. All processes disclosed have the common feature that a hydrochlorofluoroalkane is dehydrochlorinated to obtain the desired product with the number of hydrogen and chlorine atoms each reduced by one. Generally, the dehydrohalogenation of hydrochlorofluoroalkanes having at least one chlorine atom and one hydrogen atoms at carbon atoms next to each other proceeds via a dehydrochlorination yielding respective unsaturated products wherein the number of chlorine atoms and the number of hydrogen atoms are each reduced by one.

Despite the fact that hydrochlorofluoroalkenes might be subject to restrictive regulations in the foreseeable future in accordance with the Montreal protocol, there is still a need for new compounds of this type as well as for easy and safe processes for their manufacture.

It was thus an object of the present invention to provide a process for the manufacture of hydrochlorofluoroalkenes and certain novel hydrochlorofluoroalkenes which may be obtained in the process in accordance with the instant invention.

This object is achieved with the process in accordance with claim 1.

Thus, according to one aspect of the invention, a process is provided for the selective dehydrofluorination of hydrochlorofluoroalkanes comprising at least one chlorine atom and at least one fluorine atom and at least one hydrogen atom at the carbon atom or atoms vicinal to the carbon atom or carbon atoms carrying the chlorine and fluorine atoms, by subjecting said hydrochlorofluoroalkanes to a reaction at a temperature above 50° C. with an effective amount of a catalytically active metal compound selected from the group consisting of $AlF_{3-\delta}$, $MgAl_xF_{2+3x-\delta}$ and $MgZr_yF_{2+4y-\delta}$, wherein x and y have, independently of one another, values in the range of from 0 to 0.33 and $\delta$ has a value in the range of from 0 to 0.1. Preferred embodiments of the invention are set forth in the dependent claims and the detailed description hereinafter.

Novel hydrochlorofluoroalkenes are set forth in independent claim 7 and preferred embodiments thereof in the claims dependent on claim 7 and the detailed description hereinafter.

Thus, the instant invention relates to a process for the selective dehydrofluorination of hydrochlorofluoroalkanes, said hydrochlorofluoroalkanes comprising at least one chlorine atom and at least one fluorine atom and at least one hydrogen atom at the carbon atom or atoms vicinal to the carbon atom or carbon atoms carrying the chlorine and fluorine atoms.

The hydrochlorofluoroalkanes are not subject to further restrictions as far as their structure is concerned, i.e. any representative of this class of products fulfilling the foregoing prerequisites are suitable for use in the process in accordance with the instant invention.

Generally, the chlorine and fluorine substituents may be located at the same or different carbon atoms in the molecule. If a chlorine and a fluorine substituent are present at different carbon atoms, the hydrogen atoms at carbon atoms vicinal thereto might be attached to different carbon atoms or to the same carbon atom in case at least one chlorine and fluorine substituent are attached to different carbon atoms separated by one carbon atom carrying such hydrogen substituent. In this case, one hydrogen substituent in the molecule is sufficient.

Dehydrohalogenation reactions require this structural feature as in the reaction a hydrogen halide is split off, the hydrogen and the halogen arising from vicinal or neighbored carbon atoms.

Preferred hydrochlorofluoroalkanes which are suitable as educts for the process in accordance with the instant invention comprise either at least one structural element Ia and at least one structural element Ib or at least one structural element II

(Ia)

(Ib)

(II)

The substituents not shown in the formulae above are preferably selected from $C_1$-$C_8$-alkyl groups, which may be substituted by halogen, in particular by chlorine or fluorine.

A particularly preferred group of hydrochlorofluoroalkanes has the formula III

(III)

wherein $R^1$ to $R^4$ are the same or different and independently of each other represent a hydrogen atom, a fluorine atom a $C_1$-$C_8$-alkyl, a $C_1$-$C_8$-fluoroalkyl or a $C_1$-$C_8$-hydrofluoroalkyl group.

Hydrochlorofluoroalkanes having 1 to 6 carbon atoms and preferably 1 to 4 carbon atoms are preferred substrates. 3-chloro-1,1,1,3-tetrafluorobutane is a particularly preferred substrate.

Even more preferably, the substituents $R^1$ to $R^4$ are selected such that the novel hydrochlorofluoroalkenes in accordance with claim 7 and the detailed description hereinafter can be obtained from the respective starting materials. Particularly preferred are starting materials where at least one of $R^1$ or $R^2$ or $R^3$ is hydrogen.

The starting materials which can be used in the process according to the instant invention are known to the skilled man and are available from various sources. 3-chloro-1,1,1,3-tetrafluorobutane (also referred to as HCFC-364mfb according to the generally used nomenclature system used for halogenated hydrocarbons), for example, is inter alia disclosed in U.S. Pat. No. 7,074,434 and other suitable starting materials are described elsewhere.

Various routes for the manufacture of halogenated hydrocarbons with at least 3 carbon atoms are disclosed in WO 2008/043720 to which reference is made herewith for further details.

In the process in accordance with the instant invention hydrochlorofluoroalkanes as described hereinbefore are subjected to a reaction at a temperature preferably above 50° C. with an effective amount of a catalytically active metal compound selected from the group consisting of $MgF_{2-\delta}$, $AlF_{3-\delta}$, $MgAl_xF_{2+3x-\delta}$ and $MgZr_yF_{2+4y-\delta}$ wherein x and y have, independently of one another, values in the range of from 0.01 to 0.33 and $\delta$ has a value in the range of from 0 to 0.1.

Surprisingly it has been found that these catalytically effective metal compounds in this reaction yield the dehydrofluorinated products with a very good selectivity, which is typically at least 80, preferably at least 90%, the remainder being the dehydrochlorination products.

Depending on the starting materials more than one dehydrofluorination product and/or more than one dehydrochlorination product as by-product may be obtained and in this case the selectivity is expressed based on the aggregate amount of dehydrofluorination respectively dehydrochlorination products.

Particularly preferably, the selectivity towards dehydrofluorinated products vs. dehydrochlorinated products is at least 95%, most preferred above 98% and may be 100%, i.e. no detectable dehydrochlorination product in particular cases.

It was surprising and unexpected that hydrochlorofluoroalkanes would undergo a dehydrofluorination instead of a dehydrochlorination as chlorine atoms are generally the better leaving group than fluorine atoms in molecules of the respective type and thus the skilled man would have expected a completely different product spectrum.

The catalytically active metal compound is selected from the group consisting of $AlF_{3-\delta}$, $MgAl_xF_{2+3x-\delta}$ and $MgZr_yF_{2+4y-\delta}$ wherein x and y have, independently of one another, values in the range of from 0.01 to 0.33 and $\delta$ has a value in the range of from 0 to 0.1.

In the course of the extensive research conducted it has been found that the selectivity, in particular for the mixed fluorides, is very sensitive to the combination of metals. Replacing Zr or Al by e.g. V, Cr, Ni or Fe leads to a significant reduction of the selectivity, generally less than 80% towards dehydrofluorination over dehydrochlorination and to selectivities as low as approximately 40% towards dehydrofluorination e.g. in the case of $MgFe_{0.1}F_{2.3}$ or $MgNi_{0.2}F_{2.4}$ the remainder of the products being dehydrochlorination products. Commercially, such processes are disadvantageous as the required purification of the reaction mixtures is time and cost consuming.

Whereas $MgF_{2-\delta}$ generally yields lower conversions in the process and selectivities which show a certain dependency on the pre-treatment of the catalytically active compound compared to $AlF_{3-\delta}$ or the mixed fluorides, selectivities of 90% towards hydrofluorination are nevertheless achievable with a conversion of more than 80% with a suitable pretreatment as explained in more detail hereinafter. As the mixed fluorides or $AlF_{3-\delta}$ generally lead to conversions of more than 90% and selectivities of more than 95% in most cases, these compounds are particularly suitable for use in the process in accordance with the instant invention.

Preferably, x or y have a value in the range of from 0.01 to 0.25, more preferably in the range of from 0.05 to 0.20 and even more preferred in the range from 0.07 to 0.15.

$AlF_{3-\delta}$ is especially preferred, in particular respective products with a high surface area.

Respective products and processes for their manufacture have been described in WO 2004/060806 and EP 1,666,411, which are incorporated herein by reference. Such processes are also known as fluorolytic sol-gel synthesis. The mixed fluorides of Magnesium as well as the $MgF_{2-\delta}$ can be obtained in an analogous manner as described in the said references.

In accordance with a preferred embodiment of the process of the instant invention, the catalytically active metal compound is obtainable by a) providing a precursor, optionally on a support, wherein the precursor comprises a structure having the formula $AlF_{3-\delta-d}B_dL_e$, $MgAl_xF_{2+3x-\delta-d}B_dL_e$ or $MgZrF_{2+4y-\delta-d}B_dL_e$ and b) reacting the precursor with a fluorinating agent generating the catalytically active metal compound, wherein B is a co-ordinately bound group; L is an organic solvent; x and y, independently of one another, have values in the range of from 0 to 0.33, d is any integer in the range of from 0 to 3, e has a value in the range of from 0 to 1 and $\delta$ has a value in the range of from 0 to 0.1, provided that the denominator representing the number of fluorine atoms is positive.

B is preferably an alkoxide, enolate or carboxylic acid group, more preferably an alkoxide group of the formula —O—$C_cH_{2c+1}$ wherein c is any integer from 1 to 6, preferably of from 1 to 3; L is a solvent, preferably an anhydrous organic solvent selected from the group comprising alcohols, ethers, ketones, alkanes and aromatics; and d and e are preferably less than or equal to 1.

According to WO 2004/060806, the precursor is preferably obtained by reacting $M^{z+}B_z$, wherein B is preferably an alkoxide. If the metal M is aluminum, B is more preferably propoxide, dissolved or suspended in an organic solvent L, with of from 2 to 4 equivalents, preferably about 3 equivalents (preferably anhydrous) HF. The HF is preferably dissolved in an organic solvent L', whereby L' can be any of the solvents L and also L' can be equal to or different from L; followed by removing excessive solvents under vacuum at temperatures equal to or less than 350° C., preferably equal to or less than 200° C., still more preferably equal to or less than 100° C. The product obtained thereby is a precursor as defined above.

The preparation of the precursor is preferably performed in a water free solvent, preferably selected from the group consisting of alcohols, ethers, ketones, alkanes, petroleum ether, formic acid, acetic acid or propionic acid. Alcohols of formula $C_cH_{2c+1}OH$ with c=1 to 6, especially 1 to 3, are preferred.

The precursor obtained thereby, in a second step, is further fluorinated, (or "activated") with a suitable fluorinating agent. Preferred fluorinating agents are gaseous and are used at elevated temperatures. By way of example hydrofluorocarbons or hydrofluorochlorocarbons, especially $CHClF_2$, $CH_2F_2$ or 3-Chloro-1,1,3-tetrafluorobutane may be mentioned here in addition to gaseous HF. The temperatures in step b) are generally up to 350° C., preferably in the range of from 50° C. up to 300° C., more preferably in the range of from 75° C. up to 250° C. The fluorinating agent is preferably admixed with an inert gas such as nitrogen or argon, whereby up to 95% by volume inert gas can be used.

The suitable catalytically active metal compounds used in the process according to the invention can be prepared as described above by selecting the appropriate precursors.

The following detailed description sets forth various aspects of the process in accordance with the instant invention by reference to aluminum fluoride, which is particularly preferred. However, the process according to the invention can be carried out with any catalytically active metal compound as defined in claim 1 and in the description hereinbefore. Thus, in such case, aluminum fluoride may be replaced by any of the other catalytically active compounds in the embodiments described hereinafter.

In a preferred embodiment, the metal fluoride consists essentially of aluminum fluoride. The term "essentially" denotes preferably that the content of other amorphous metal fluorides is equal to or less than 3% by weight, still more preferably equal to or less than 2% by weight.

WO 2004/060806 discloses another embodiment wherein $M^{z+}F_{(z-\delta)-d}B_d$ is used as starting material, and which is not coordinated with a solvent.

In another embodiment, if desired, the aluminum fluoride can be doped with metal fluorides of zinc, tin, copper, chromium, vanadium, iron, or magnesium, although non-doped materials are preferred.

Details and examples for the preparation of high surface area metal fluorides are given in WO 2004/060806, which for this purpose is herewith incorporated by reference.

Amorphous aluminum fluoride is the preferred metal fluoride. The process of the present invention yields the dehydrofluorinated products in good yield and good selectivity.

Aluminum fluorides as obtained by the processes in accordance with WO 2004/060806 and EP 1,666,411 and as described in preferred embodiments hereinbefore have generally a very high surface area, preferably in the range of from 100 to 300 m²/g, as measured according to the BET method using $N_2$ (see [0091] of US2006/052649 A1 for details). Particularly preferred the surface area of the aluminium fluorides thus obtained is in the range of from 180 to 280 m²/g.

Furthermore, aluminum fluorides thus obtained are generally X-ray amorphous as can be determined by X-ray powder diffractometry in accordance with known methods.

The aluminum fluorides can also have lower surface areas. In this case good results have been obtained with products having surface areas in the range of from 5 to 200, in particular of from 10 to 150 m²/g.

The metal fluorides described before are generally strong Lewis acids and are essentially free of Cl. The term "X-ray amorphous" or amorphous denotes that the microcrystalline domains of the solid matter, i.e. the amorphous metal fluoride, generally have a size of less than or equal to 50 nm, preferably in the range of from 20 to 50 nm. Preferably the amorphous metal fluoride is present in the form of very small solid particles which may be preferably partially agglomerated to form bigger particles.

Amorphous $AlF_3$, preferably with a high surface as referred to above (hereinafter $HS-ALF_3$), carried on a support, is highly suitable for use in the process of the present invention.

Preferably, a support is selected which has a suitably shaped form, is chemically and thermally stable under the conditions of catalyst synthesis and under reaction conditions of catalyst use, mechanically stable, not deteriorating the performance of the catalyst, not interfering with the catalyzed reaction, and enabling anchoring of $HS-AlF_3$. Any support which meets these requirements can be used. For example, oxides, fluorides and oxifluorides of aluminum or of transition metals are very suitable. Usually, these are present in crystalline form. Activated carbon can also be applied; in a preferred embodiment, aluminum oxide or aluminum fluoride is used as support; in a more preferred embodiment aluminum oxide is used, and in an even more preferred embodiment $\gamma-Al_2O_3$ is used as support. In this case, the supported metal fluoride is high surface metal fluoride on $\gamma-Al_2O_3$.

Very preferably, the supported amorphous metal fluoride catalyst is $HS-AlF_3$ on a support, e.g., $HS-AlF_3$ on $\gamma-Al_2O_3$. If desired, the aluminum fluoride can be doped with one or more other metal fluorides, for example, the fluorides of zinc, tin, copper, iron, chromium, vanadium or magnesium, although undoped products are generally preferred. Such doped supported catalysts can be prepared by adding hydrolysable metal compounds, for example, the metal alkoxides to the hydrolysable aluminum compound.

Preferably, the total amount of coated amorphous metal fluoride, especially of $AlF_3$ in the supported catalyst is equal to or greater than 3% by weight, more preferably equal to or more than 4% by weight. Preferably, the content of aluminum fluoride in the supported catalyst is equal to or less than 30% by weight, more preferably equal to or less than 20% by weight. In some applications, the content can be equal to or less than 10% by weight. A range with good results is between 4 and 20% by weight. A range of 4 to 8% by weight also gives good results.

It is known from EP 1666411 that the Lewis acidity of amorphous high surface area aluminum fluoride becomes reduced upon partial substitution of fluoride by oxide. Consequently, if formation of oxyfluoride is to be avoided, reducing adsorbed water and/or inherent OH-groups of the support by thermal pre-treatment preserves the Lewis acidity, i.e. the catalytic performance of the anchored $HS-AlF_3$, i.e. of the final catalyst. Therefore, the support, e.g. $g-Al_2O_3$, is preferably heated prior to the coating procedure. Heating is preferably performed for equal to or less than 48 hours, preferably equal to or less than 12 hours, advantageously at temperatures which do not result in undesired transformation of the support. For example, it is avoided to transform $\gamma-Al_2O_3$ into $\alpha-Al_2O_3$ (which can be determined by X-ray powder diffraction). For example, $\gamma-Al_2O_3$ can be heated to temperatures between 400° C. and 900° C. Preferably, it is heated to a temperature equal to or higher than 600° C. Preferably, it is heated to a temperature equal to or lower than 900° C. in air and subsequently cooled down to room temperature under exclusion of moisture.

The coating procedure can be performed in a manner principally known to prepare catalytic coatings on catalyst supports. Two specific alternatives are preferred. Both alternatives comprise a step wherein a support coated with the precursor is formed, and a step wherein the activation takes place.

Alternative a): According to the first preferred alternative, the support is impregnated with the aluminum compound $Al^{z+} B_z$; B and z have the meanings given above. After impregnation, the sol-gel reaction with HF, preferably applied in a solvent, is performed to obtain the precursor.

In detail, the support, preferably thermally pretreated $\gamma\text{-Al}_2O_3$, is given, preferably under stirring, to a solution of a suitable organic aluminum compound, preferably an aluminum alkoxide, more preferably aluminum isopropoxide or methoxide, in an anhydrous organic solvent, preferably an alcohol. If a doped supported catalyst is to be produced, a suitable organic metal compound of the respective metal or metals is added. Contact between support and aluminum compound, preferably under stirring, is continued for a sufficient time to achieve the desired degree of impregnation. For example, after addition of the aluminum compound, the contact can be continued for equal to or more than 10 minutes, preferably, for equal to or more than 20 minutes. The contact can be extended, if desired, to a very long time, for example, more than 6 hours. It is assumed that the longer the contact, the deeper the aluminum compound or precursor will penetrate into the support. Preferably, the contact between support and aluminum compound is equal to or less than 6 hours, still more preferably, equal to or less than 2 hours. Often, 20 minutes to 45 minutes are very suitable.

Then, $Al^{z+} B_z$ is reacted with HF to transform it into the precursor. A solution of anhydrous hydrogen fluoride in an organic solvent, preferably in an $C_1$ to $C_3$ alcohol or in diethyl ether, is added, preferably under continued stirring, to the system of support and aluminum compound $Al^{z+} B_z$. The amount of HF is selected so that the molar ratio of HF:Al is preferably equal to or greater than 2. Preferably, it is equal to or lower than 4. Very preferably, the molar ratio of HF:Al is $3\pm0.1$.

Preferably, the total amount of aluminum compound starting material (which is converted to the $HS\text{-AlF}_3$ phase) in the system is adjusted to correspond to an $AlF_3$ content of the final catalyst of equal to or greater than 3% by weight, more preferably equal to or more than 4% by weight. Preferably, the content of aluminum fluoride in the supported catalyst is equal to or less than 30% by weight, more preferably equal to or less than 20% by weight, sometimes even equal to or less than 10% by weight, based on the weight of the catalyst. Often, the amount is adjusted so that the content of the $HS\text{-AlF}_3$ phase in the supported catalyst is preferably between 4 and 20% by weight. Often, a supported catalyst with 4 to 8% by weight $HS\text{-AlF}_3$ is produced.

Alternative b): According to the second preferred alternative, the organic metal compound, preferably the aluminum compound, preferably in the form of a solution, is first reacted in the sol-gel type reaction with the appropriate amount of HF solution, preferably under stirring, followed by addition of the respective support, whereby the materials used and their relative amounts are as described above, especially in view of the alternative a).

After the reaction of the aluminum compound and HF to form the precursor has taken place, be it after impregnation of the carrier according to the first alternative, or before contact with the carrier according to the second alternative, excessive solvent(s) is or are removed. Preferably, this is performed in a gentle manner, preferably under vacuum. The removal advantageously is supported by warming or heating. Preferably, the temperature is equal to or higher than 25° C., more preferably, it is equal to or higher than 30° C. Preferably, the temperature is equal to or lower than 200° C., more preferably, it is equal to or lower than 150° C. A preferred range is 40 to 90° C. Both procedures a) or b) and subsequent solvent removal provide a supported precursor.

The precursor already has catalytic activity. The catalytic activity can be greatly enhanced if the precursor is activated by subsequent fluorination with a gaseous fluorinating agent at elevated temperature, for example, with one or more hydrochlorofluorocarbons or hydrofluorocarbons, especially with 1 to 4 carbon atoms, or with HF. The fluorinating agent is preferably admixed with an inert gas such as nitrogen or argon, whereby of from 10 up to 95 vol. % inert gas can be used.

In a preferred manner, the activation is performed applying
A1) $CCl_2F_2$, $CHClF_2$ or $CH_2F_2$ or $CHF_3$ or $CH_3F$ or 3-chloro-1,1,1,3-tetrafluorobutane, or
A2) gaseous HF; followed optionally by
B) flushing with inert gas, preferably nitrogen or a noble gas, for example, argon,
providing a highly Lewis acidic supported $HS\text{-AlF}_3$ catalyst, preferably on $\gamma\text{-Al}_2O_3$ of the formula $AlF_{3-\delta}/\gamma\text{-Al}_2O_3$.

In the first alternative, $CHClF_2$ and 3-chloro-1,1,1,3-tetrafluorobutane are the preferred fluorinating agents. They can be applied in admixture with up to 95% (v/v), of an inert gas such as nitrogen or a noble gas, preferably argon; the content of the inert gas is preferably equal to or higher than 75% (v/v); it is preferably equal to or lower than to 90% (v/v). Especially preferably, the inert gas content is $83\pm2\%$ (v/v). The temperature in step A1) preferably is equal to or higher than 150° C., more preferably, equal to or higher than 180° C. Preferably, the temperature is equal to or lower than 400° C.

In the alternative step wherein HF is used as fluorinating agent, the temperature during treatment is preferably equal to or lower than 200° C.; preferably, it is equal to or higher than 90° C. A temperature range from 75° C. to 150° C. is very preferred, still more a range from 110° C. to 130° C. HF preferably is diluted with equal to or more than 80% (v/v) of an inert gas, for example, nitrogen or a noble gas, preferably argon. Preferably, the inert gas content is equal to or less than 97.5% (v/v). An especially preferred content of inert gas is in the range of $95\pm2\%$ (v/v) of inert gas.

In a subsequent step, flushing is optionally performed to remove volatiles from the catalyst. It is preferred to perform a flushing step. Flushing can be stopped when the desired degree of purification has been achieved. It can be performed for an extended time, for example, up to ten hours or more. Preferably, flushing is performed for equal to or less than 6 hours. Preferably, it is performed for equal to or more than 1 hour. The temperature during flushing is preferably equal to or higher than 200° C. Preferably, it is equal to or lower than 300° C. A temperature range of from 240° C. and 260° C. is very suitable. This is especially advantageous if the activation was performed using HF.

It is to be noted that the manufacture of supported catalysts as described before is also applicable to other metal fluorides and especially to mixtures of different metal fluorides resulting in doped systems.

The supported catalyst can be prepared in the form of a powder, in the form of pellets, beads, extrudates and other formed bodies. Beads with a diameter in the range of, for example, 1 to 10 mm are very suitable for the dehydrofluorination process according to the instant invention.

The dehydrofluorination reaction in the process of the present invention takes place very selectively and in high yields. The temperature at which dehydrofluorination occurs depends from the respective starting compound. Generally, the reaction temperature is equal to or higher than 50° C., preferably equal to or higher than 150° C. The reaction can be performed at even lower temperature, but in some cases, the speed of reaction may be considered to be too low. Generally, the reaction is performed at a temperature equal to or lower than 500° C., preferably equal to or lower than 450° C., and very preferably equal to or lower than 420° C. The catalyst is very active for extended periods of time when the reaction temperature is equal to or lower than 400° C. The result of the dehydrofluorination is very good at temperatures e.g. above 100° C. The long-term performance of the catalyst is especially good if it is operated at temperatures equal to or below 400° C.

The reaction temperature is preferably equal to or higher than 150° C. The speed of reaction can be accelerated if the reaction temperature is equal to or higher than 200° C. Often, performing the reaction in a range of from 300° C. to 400° C. allows a high reaction speed with high conversion. A fast reaction and high conversion are observed even if the dehydrofluorination temperature is equal to or higher than 400° C. It may be equal to or lower than 500° C.

Depending on the structure of the starting material in the dehydrofluorination isomers may be formed, which can then be separated by distillation, if required. In the dehydrofluorination of HCFC-364 having the formula $CH_3$—$CFCl$—$CH_2$—$CF_3$, for example, three isomers are formed namely 3-chloro-1,1,1-trifluorobut-3-ene and the E- and Z-isomers of 3-chloro-1,1,1-trifluoro-but-2-ene. With other starting materials the respective isomers can be obtained.

In some cases, the balance between high reaction speed and high selectivity may favour operation at relatively low reaction temperature.

If one observes diminishing catalyst activity, e.g. after long reaction periods, or if the reaction temperature was selected too high, a regeneration of the catalyst is possible. Oxidizing gases can be passed at elevated temperatures through the reactor, e.g. air or oxygen. As is described below, the catalytic activity can be extended by passing a hydrofluorocarbon/nitrogen (or inert gas) mixture through the reactor.

The reaction can be performed batch wise or continuously. It is preferred to operate in the gas phase, especially continuously.

If desired, the halogenated hydrocarbon used as starting material can be diluted before the dehydrofluorination reaction with an inert gas, for example, nitrogen, or a noble gas, for example, argon. In this case, the halogenated hydrocarbon preferably is present in the gas mixture with inert gas in an amount of equal to or more than 10 vol. %. Preferably, it is present in an amount of equal to or less than 75 vol. %, more preferably in an amount of equal to or less than 50 vol. %, and especially preferably equal to or less than 35 vol. %. The productivity of the catalyst was in some cases observed to be higher when using inert gas (nitrogen for example).

Accordingly, mixtures comprising or consisting of nitrogen and a hydrochlorofluoroalkane with 2 to 5 carbon atoms in a molar ratio of $N_2$:hydrochlorofluoroalkane of (2-9):1, preferably of (3-6):1 can be passed over the catalyst as described above. Mixtures comprising or consisting of nitrogen and a hydrochlorofluoroalkane with 2 to 5 carbon atoms in a molar ratio of $N_2$:hydrochlorofluoroalkane of (3-5):1 are especially preferred. Especially preferred are mixtures comprising or consisting of $N_2$ and a $C_3$ or $C_4$ hydrochlorofluoroalkane in a molar ratio of (2-9):1, preferably (3-6):1, more preferably (3-5):1.

Certain hydrochlorofluoroalkenes obtainable with the process of the present invention are novel and constitute a further aspect of the present invention.

The novel hydrochlorofluoroalkenes have the formula IV

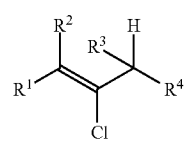

(IV)

wherein the following relationship exists between the number of carbon atoms ($N_C$), the number of hydrogen atoms ($N_H$), the number of chlorine atoms ($N_{Cl}$) and the number of fluorine atoms ($N_F$):

$N_C \geq 4$ $N_F \geq N_H - 1$ $N_F \geq N_{Cl} + 2$ and $R^1$, $R^2$, $R^3$ and $R^4$, independently of each other represent a hydrogen atom, a fluorine atom, a $C_1$-$C_8$-alkyl-, a $C_1$-$C_8$-halooalkyl or a $C_1$-$C_8$ hydrohaloalkyl group.

The novel unsaturated hydrochlorofluoroalkenes according to the instant invention contain at least one chlorine atom attached to a carbon atom connected to a neighbouring carbon atom through a double bond.

Furthermore, the novel hydrochlorofluoroalkenes comprise at least 4 carbon atoms, i.e. of the substituents $R^1$, $R^2$, $R^3$ and $R^4$ is not fluorine or hydrogen, i.e. at least one alkyl or halogenalkyl substituent is present.

Preferred compounds are those wherein the substituents R are selected from chlorine-free groups, preferably alkyl, fluoroalkyl or hydrofluoroalkyl.

Preferred hydrochlorofluoroalkenes in accordance with the present invention are those where a hydrogen substituent is present at both carbon atoms neighbouring the carbon atom bearing the chlorine substituent.

A particularly preferred group of hydrochlorofluoroalkenes according to the invention comprises the structural element V

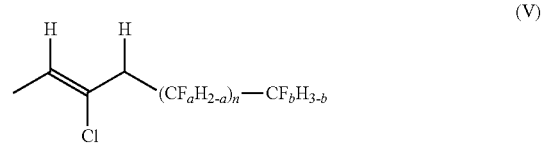

(V)

where n stands for an integer of from 0 to 5, preferably of from 0 to 4 and particularly preferred of from 0 to 3, a is 0, 1 or 2 and b is 1, 2 or 3.

If n in the above formulae is greater than one, then a may take different values at different carbon atoms.

Preferred hydrochlorofluoroalkenes according to the instant invention comprise 4, 5 or 6 carbon atoms and at least 3 fluorine atoms. The remaining atoms to saturate the valencies of the carbon atoms in the molecule are selected from chlorine and hydrogen.

Hydrochlorofluoroalkenes according to the invention with 4 carbon atoms and 1 chlorine atom are the following:
2-chloro-4,4,4-trifluorobut-1-ene, 2-chloro-3,4,4,4-tetrafluorobut-1-ene,
2-chloro-3,4,4-trifluorobut-1-ene, 2-chloro-1,4,4,4-tetrafluorobut-1-ene, 2-chloro-1,4,4-trifluorobut-1-ene, 2-chloro-1,3,4,4,4-pentafluorobut-1-ene,
2-chloro-1,3,4,4-tetrafluorobut-1-ene, 2-chloro-1,3,4-trifluorobut-1-ene,
2-chloro-1,1,4,4,4-pentafluorobut-1-ene, 2-chloro-1,1,3,4,4,4-hexafluorobut-1-ene,
2-chloro-1,1,4,4-tetrafluorobut-1-ene, 2-chloro-1,1,3,4,4-pentafluorobut-1-ene,
2-chloro-1,1,4-trifluorobut-1-ene, 2-chloro-1,1,3,4-tetrafluorobut-1-ene,
2-chloro-1,1,3-trifluorobut-1-ene, particularly preferred being 2-chloro-4,4,4-trifluorobut-1-ene (also referred to as 3-chloro-1,1,1-trifluorobut-3-ene).

Exemplary for hydrochlorofluoroalkenes with 5 carbon atoms and 1 chlorine atom and preferably with only hydrogen as substituent at carbon atom 1 are
2-chloro-3,4,4,5,5,5-hexafluoropent-1-ene, 2-chloro-3,4,4,5,5-pentafluoropent-1-ene,
2-chloro-3,4,4,5-tetrafluoropent-1-ene, 2-chloro-3,4,5,5,5-pentafluoropent-1-ene
2-chloro-4,4,5,5,5-pentafluoropent-1-ene and 2-chloro-4,4,5,5-tetrafluoropent-1-ene.

According to the required ratio between the number of fluorine atoms and the number of hydrogen atoms, it is obvious for the skilled man that hydrochlorofluoroalkenes according to the instant invention with 4 carbon atoms must have at least three, those with 5 carbon atoms at least 4 and those with 6 carbon atoms at least 5 fluorine atoms if there is not more than one chlorine atom in the molecule.

The number of chlorine atoms in the molecule is at maximum the number of fluorine atoms minus 2, which, again evident for the skilled man leads to the result that for example hydrochlorofluoroalkenes according to the instant invention with 4 carbon atoms and 3 fluorine atoms can only comprise one chlorine atom (formula $C_4H_4ClF_3$) and at maximum, if the molecule contains one or two hydrogen atoms, 2 chlorine atoms (formula $C_4HCl_2F_5$ or $C_4H_2Cl_2F_4$). Due to the known change of properties with regard to ozone depletion potential and global warming potential with increasing number of chlorine atoms, hydrochlorofluoroalkenes where the number of chlorine atoms is on the lower side, are generally preferred. Specifically, hydrochlorofluoroalkenes according to the instant invention with 4 carbon atoms contain preferably only 1 chlorine atom, those with 5 carbon atoms not more than 2 chlorine atoms.

The novel hydrochlorofluoroalkenes according to the instant invention can be applied as such, e.g. as solvents. They may also be applied as intermediates in chemical reactions. They possess interesting properties making them particularly useful as starting materials for chlorination processes with chlorine or tetrachloromethane and subsequent substitution of chlorine by fluorine by virtue of a fluorination reaction, generally with HF as fluorinating agent. The resulting products, hydrofluoroalkanes, i.e. hydrocarbons containing only hydrogen, fluorine and carbon atoms have found widespread use as a replacement for chlorinated hydrocarbons which have a negative influence on the ozone layer of the atmosphere and are thus subject to a potential phase-out in accordance with the Montreal protocol. The hydrofluoroalkanes so obtained can further be converted to hydrofluoroalkenes by dehydrofluorination.

As an exemplary route to hydrofluoroalkenes, the hydrochlorofluoroalkenes of the instant invention can be reacted in a first step with e.g. $Cl_2$ or tetrachloromethane to obtain saturated hydrochlorofluoroalkanes, which subsequently can be converted to hydrofluoroalkanes by reaction with hydrogen fluoride under conditions known to the skilled man and described in the literature. In a final step. If desired, the hydrofluoroalkanes can be dehydrofluorinated to obtain hydrofluoroalkenes. Again, the respective processes are known to the skilled man and described in the literature, so there is no detailed description necessary here.

Accordingly, one preferred aspect of the present invention concerns the use of the novel hydrochlorofluoroalkenes of formula (IV) and (V) for the manufacture of hydrofluoroalkanes or hydrofluoroalkenes. Preferred compounds to be used in this aspect are given above, especially those exemplified above having four carbon atoms and one chlorine atom, and those having five carbon atoms and one chlorine atom given above.

Should the disclosure of any patents, patent applications, and publications which are incorporated herein by reference conflict with the description of the present application to the extent that it may render a term unclear, the present description shall take precedence.

EXAMPLES

The catalytically active metal compounds were prepared in accordance with the so-called water-free fluorolytic Sol-Gel method in accordance with Kemnitz, E. et al., "Amorphe Metallfluoride mit aussergewöhnlich grosser spezifischer Oberfläche", Angew. Chem. 2003, 115(35) and Rüdiger, S. and Kemnitz, E., "The fluorolytic sol-gel method to metal fluorides—a versatile process opening up a variety of application fields, Dalton Trans. 2008, pp. 1117-1127.

In the first step a respective metal organic precursor compound was reacted with HF in methanol. Thereby sol- or gel-like network structures were obtained. Thereafter the volatile substances were removed by drying at 100° C. and reduced pressure for two hours.

The resulting Xerogel was then subjected to a gas-phase fluorination with either $CHClF_2$ (S-22) or 3-chloro-1,1,1,3-tetrafluorobutane (S-364).

The fluorination with S-22 was conducted as described below:

The reactor used for the fluorination with S-22 was a tubular quartz glass reactor with an internal diameter of 8 mm. 1.2 g of the respective metal compound was filled into the reactor, resulting in a 3-4 cm height of material. The bed of the precursor was fixed in the reactor with a plug of quartz wool. A mixture of nitrogen gas (20 ml/min) and S-22 (5 ml/min) were introduced into the reactor at the temperatures and for the times indicated in table 1. The fluorination was stopped once a conversion of the precursor of more than 90% was achieved or if no increase of the conversion could be measured for a period of one hour for the mixed fluorides and of 30 min. for the aluminum fluorides used. The conversion of the precursor at the end of the reaction is also given in table 1.

In addition a catalyst comprising 15 wt % $AlF_3$ on a support of $\gamma$-$Al_2O_3$ and $\beta$-$Al_2O_3$ were used for the catalytic reaction. These catalysts were not subjected to fluorination before catalysis.

Table 1 shows the times the fluorination was carried out at the temperature indicated in hours.

TABLE 1

| Precursor | Temperature (° C.) | | | | | | |
|---|---|---|---|---|---|---|---|
| | 150 | 200 | 230 | 250 | 300 | 330 | 350 |
| $AlF_3$ | 2 h | 2 h | 2.5 h 96% | — | — | — | — |

TABLE 1-continued

| Precursor | Temperature (° C.) | | | | | | |
|---|---|---|---|---|---|---|---|
| | 150 | 200 | 230 | 250 | 300 | 330 | 350 |
| 2% Na—AlF$_3$ | 2 h | 2 h | 2 h 79% | — | — | — | — |
| MgAl$_{0.1}$F$_{2.3}$ | — | 2 h | — | 2 h | 1 h 93% | — | — |
| MgZr$_{0.1}$F$_{2.3}$ | — | 2 h | — | 2 h | 2 h | 2 h | 2 h 32% |
| MgF$_2$ | — | 2 h | — | 2 h | 2 h | 2 h | 3 h 3% |

The catalytically active compounds obtained after fluorination with S 22 as above are hereinafter designated by the prefix S 22.

The catalytic dehydrofluorination of 3-chloro-1,1,1,3-tetrafluorobutane (S-364) was carried out as follows:

A heatable quartz reactor having an internal diameter of 8 mm and an external diameter of 10 mm was filled with 200 mg of the respective catalytically active compound which was fixed in the middle of the reactor by quartz wool plugs. A gas stream of 25 ml/min of a mixture of 3-chloro-1,1,1,3-tetrafluorobutane and nitrogen (volume ratio 1:4) was introduced into the reactor which was kept at a temperature of 200° C. After passage through the reactor, the gas stream was carried through a 0.5 molar solution of sodium hydrogen carbonate to neutralize the gaseous acids produced during the reaction (HF, SiF$_4$). Thereafter samples were taken which were analyzed directly by gas chromatography and GC-MS respectively (in this case the gas stream was condensed in trichloromethane for injection into the GC-MS system).

To evaluate the results of a prior fluorination with S-364, the untreated precursor was introduced into the reactor and subjected to a stream of gaseous S-364 (mixture with nitrogen in volume ratio 1:4) for two hours. After these two hours the products were deemed as catalysts and designated with the prefix S 364.

The fact that the conversion increased steadily in the first 120 min. was an indication of a fluorination taking place.

The dehydrofluorination of S-364 yielded a mixture of three isomers, namely cis- and trans 3-chloro.1,1,1-trifluorobut-2-ene (hereinafter referred to as CTFBE1 and CTFBE2 and 3-chloro-1,1,1-trifluoro-but-3-ene, hereinafter referred to as CTFBE3.

Table 2 shows the results of the dehydrofluorination with the various catalytically active metal compounds and the respective main product.

TABLE 2

| Catalyst | Reaction time | Conversion | Selectivity | Main product |
|---|---|---|---|---|
| S 22-AlF$_3$ | 1 h | >99% | 1.0 | CTFBE1 69% |
| S 364-AlF$_3$ | 2 h | >99% | 1.0 | CTFBE1 68% |
| S 22-2% Na—AlF$_3$ | 1 h | >99% | 1.0 | CTFBE1 64% |
| γ-Al$_2$O$_3$/AlF$_3$ | 1 h | >99% | 1.0 | CTFBE! 68% |
| β-AlF$_3$ | 1 h | >99% | 1.0 | CTFBE1 71% |
| S 364 MgF$_2$ | 2 h | 83% | 0.9 | CTFBE1 75% |
| S 22 MgAl$_{0.1}$F$_{2.3}$ | 1 h | 98% | 1.0 | CTFBE1 67% |
| S 22-MgZr$_{0.1}$F$_{2.4}$ | 1 h | 83% | 1.0 | CTFBE1 82% |

A selectivity of 1.0 in table 2 denotes the complete absence of dehydrochlorination products, whereas a selectivity of 0.9 denotes 10% of dehydrochlorination products.

The examples above show that the process in accordance with the instant invention yields a very selective dehydrofluorination instead of the expected dehydrochlorination.

If the Al in S-22 MgAl$_{0.1}$F$_{2.3}$ is substituted by the respective amount of Fe(III), the selectivity drops to 0.63 and if the Al is replaced by Cr the selectivity drops to 61% which shows the importance of the metal in the mixed fluorides.

All catalysts yield as main product the same isomer in about the same amount.

Further embodiments of the instant invention by modifying the reaction conditions or the compositions of the catalytically active metal compound are evident to the skilled man.

The invention claimed is:

1. A process for the selective dehydrofluorination of a hydrochlorofluoroalkane, said hydrochlorofluoroalkane comprising a carbon atom or carbon atoms carrying at least one chlorine atom and at least one fluorine atom, and further comprising at least one hydrogen atom at a carbon atom or carbon atoms vicinal to the carbon atom or carbon atoms carrying the chlorine and fluorine atoms, said process comprising subjecting said hydrochlorofluoroalkane to a reaction at a temperature above 50° C. with an effective amount of a catalytically active metal compound selected from the group consisting of AlF$_{3-\delta}$, MgAl$_x$F$_{2+3x-\delta}$, and MgZr$_y$F$_{2+4y-\delta}$, wherein x and y have, independently of one another, values in the range of from 0 to 0.33, and wherein δ has a value in the range of from 0 to 0.1;
   wherein the catalytically active metal compound is obtained by
   a) providing a precursor, optionally on a support, wherein the precursor comprises a structure having the formula AlF$_{3-\delta-d}$B$_d$L$_e$, MgAl$_x$F$_{2+3x-\delta-d}$B$_d$L$_e$, or MgZrF$_{2+4y-\delta-d}$B$_d$L$_e$, and
   b) reacting the precursor with a fluorinating agent generating the catalytically active metal compound,
   wherein B is a co-ordinately bound group; wherein L is an organic solvent; wherein x and y, independently of another, have values in the range of from 0 to 0.33; wherein d is any integer in the range of from 0 to 3; wherein e has a value in the range of from 0 to 1; and wherein δ has a value in the range of from 0 to 0.1, provided that the denominator representing the number of fluorine atoms is positive.

2. The process in accordance with claim 1, wherein B is an alkoxide, enolate, or carboxylic acid group.

3. The process in accordance with claim 1, wherein L is selected from the group consisting of alcohols, ethers, ketones, alkanes, and aromatics.

4. The process in accordance with claim 1, wherein the fluorinating agent is selected from the group consisting of hydrogen fluoride, fluorochloroalkanes, and hydrochlorofluoroalkanes.

5. The process in accordance with claim 1, wherein the hydrochlorofluoroalkane is selected from compounds comprising at least one structural element Ia in combination with at least one structural element Ib or compounds comprising at least one structural element II

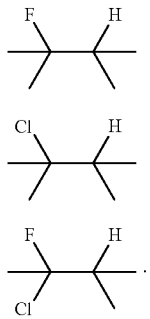

6. The process in accordance with claim 5, wherein the hydrochlorofluoroalkane comprising the at least one structural element Ia in combination with the at least one structural element Ib, or comprising the at least one structural element II, is substituted by C1 to C8 alkyl groups which are optionally substituted by halogen.

7. The method in accordance with claim 6, wherein the hydrochlorofluoroalkane has a formula III

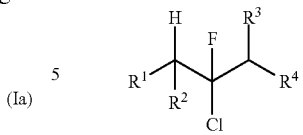

wherein $R^1$ to $R^4$ are the same or different and, independently of each other, represent a hydrogen atom, a fluorine atom a $C_1$-$C_8$-alkyl, a $C_1$-$C_8$-fluoroalkyl, or a $C_1$-$C_8$-hydrofluoroalkyl group.

8. The process in accordance with claim 1, wherein the hydrochlorofluoroalkane has from 1 to 6 carbon atoms.

9. The process in accordance with claim 8, wherein the hydrochlorofluoroalkane is 3-chloro-1,1,1,3-tetrafluorobutane.

10. The process in accordance with claim 1, wherein the catalytically active metal compound is $AlF_{3-\delta}$.

11. The process in accordance with claim 10, wherein the catalytically active $AlF_{3-\delta}$ compound is in amorphous form, or with a high surface area in the range of from 100 to 300 $m^2/g$, or both in amorphous form with said high surface area.

* * * * *